US009744078B2

(12) United States Patent
Carolan et al.

(10) Patent No.: US 9,744,078 B2
(45) Date of Patent: Aug. 29, 2017

(54) SOUND ABSORBING DEVICE OF THE TYPE ADAPTED TO COVER THE EARS OF A USER

(75) Inventors: Anthony Carolan, Sligo (IE); Rhona Togher, Sligo (IE); Eimear O'Carroll, Sligo (IE)

(73) Assignee: RESTORED HEARING LIMITED, Sligo, Co. Sligo (IE)

( * ) Notice: Subject to any disclaimer, the term of this patent is extended or adjusted under 35 U.S.C. 154(b) by 0 days.

(21) Appl. No.: 13/818,851

(22) PCT Filed: Aug. 25, 2011

(86) PCT No.: PCT/EP2011/064684
§ 371 (c)(1),
(2), (4) Date: Feb. 25, 2013

(87) PCT Pub. No.: WO2012/025608
PCT Pub. Date: Mar. 1, 2012

(65) Prior Publication Data
US 2013/0153328 A1    Jun. 20, 2013

(30) Foreign Application Priority Data

Aug. 26, 2010   (EP) .................................... 10174237

(51) Int. Cl.
| | | |
|---|---|---|
| A61F 11/14 | (2006.01) | |
| A61F 11/08 | (2006.01) | |
| A61F 11/10 | (2006.01) | |
| A61F 11/12 | (2006.01) | |

(52) U.S. Cl.
CPC .............. *A61F 11/14* (2013.01); *A61F 11/08* (2013.01); *A61F 11/10* (2013.01); *A61F 11/12* (2013.01); *A61F 2250/0034* (2013.01)

(58) Field of Classification Search
CPC ........ A42B 3/16; A42B 3/166; H04R 1/1008; A61F 11/06; A61F 11/14
USPC ............................................... 181/129; 2/423
See application file for complete search history.

(56) References Cited

U.S. PATENT DOCUMENTS

| | | | | |
|---|---|---|---|---|
| 3,432,861 | A * | 3/1969 | Flagg ................................ | 2/209 |
| 3,506,980 | A * | 4/1970 | Aileo ................................ | 2/209 |
| 3,782,379 | A |   1/1974 | Lampe | |
| 3,875,592 | A * | 4/1975 | Aileo ................................ | 2/209 |
| 4,023,642 | A * | 5/1977 | Korn ............................. | 181/175 |
| 5,815,842 | A * | 10/1998 | Hiselius ........................... | 2/209 |
| 5,920,911 | A * | 7/1999 | Cushman ......................... | 2/209 |
| 6,625,819 | B1 * | 9/2003 | Tsai ................................. | 2/209 |
| 7,198,133 | B2 * | 4/2007 | Warring et al. ............... | 181/129 |
| 2007/0163571 | A1 * | 7/2007 | Sereboff ........................ | 126/599 |
| 2010/0189277 | A1 * | 7/2010 | Birgersson .............. | A61F 11/12 |
| | | | | 381/73.1 |

FOREIGN PATENT DOCUMENTS

| | | |
|---|---|---|
| GB | 1126944 | 9/1968 |
| GB | 2340381 | 2/2000 |

OTHER PUBLICATIONS

Wikipedia Page for Thixotropy, http://en.wikipedia.org/wiki/Thixotropy, accessed Feb. 5, 2015.*

* cited by examiner

*Primary Examiner* — Jeremy Luks
(74) *Attorney, Agent, or Firm* — Occhiuti & Rohlicek LLP

(57) ABSTRACT

A sound absorbing device of the type adapted to cover the ears of a user and comprising a sound absorbing material, wherein the sound absorbing material comprises of a thixotropic material.

10 Claims, 19 Drawing Sheets

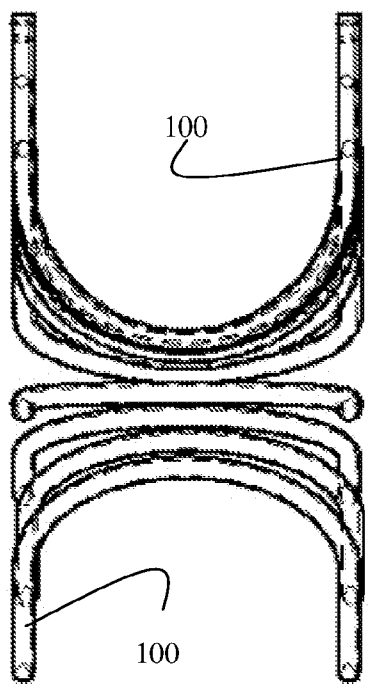 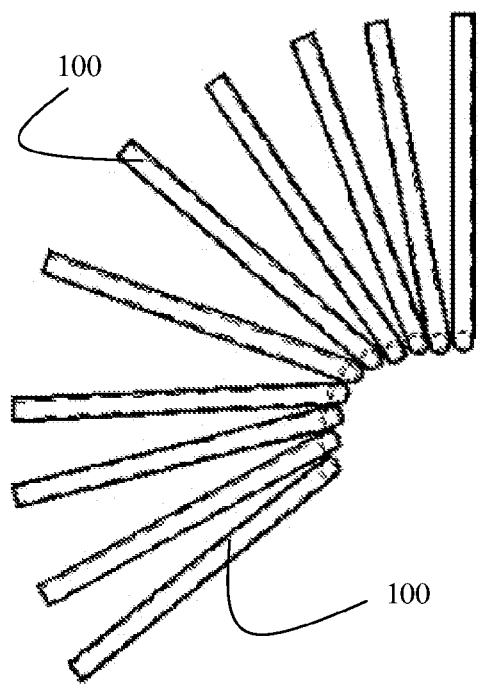
Figure 10(A)                     Figure 10(B)

SOUND ABSORBING DEVICE OF THE TYPE ADAPTED TO COVER THE EARS OF A USER

CROSS REFERENCE TO RELATED APPLICATION

This application is the national phase under 35 USC 371 of international application no. PCT/EP2011/064684, filed Aug. 25, 2011, which claims the benefit of the priority date of European application no. 10174237.7, filed Aug. 26, 2010. The contents of the aforementioned applications are incorporated herein in their entirety.

FIELD OF THE INVENTION

The present invention relates to a sound absorbing device of the type adapted to cover the ears of a user for example noise-cancelling headphones, ear plugs, or ear muffs.

BACKGROUND TO THE INVENTION

It is commonly known in the art that the ambient or background noise levels experienced by people every day may be both harmful and distracting. The noise of burglar alarms, jackhammers, buses, trains, heavy commuter traffic and construction sites in large city and urban areas can aggravate residents and commuters alike.

Users of portable music players such as MP3 players generally have the volume of their headphones raised to "block out" the ambient noise of the environment they find themselves in. Long-term use of such music players at high volumes can damage hearing. Furthermore, listening to music players at high levels when walking or cycling through city centres and urban areas inhibits other senses from functioning optimally such as being aware of traffic, other cyclists and pedestrians, which is a key sense to have functioning optimally in a busy city centre where traffic is a potential, and sometimes fatal, hazard.

Furthermore, in industry the welfare of workers who are exposed to levels of excessive noise in the workplace is important. The use of ear muffs, ear plugs and the like are commonly required by those workers to protect their hearing. However, the wearing of such ear protectors may also inhibit the wearer's awareness of their surroundings which could lead to accidents occurring in the workplace.

The use of materials in energy absorbing compositions is known, for example as disclosed in WO 2007/079320 (Sereboff). The composition is a substantially non-elastic incompressible composition, which does not quickly self-level under standard operating conditions and provides an incident energy absorbing property, wherein the incident energy may include sound energy. The applicants of WO 2007/079320 also claim that the composition may be used as an effective barrier against low frequency, high-energy sound in, for example, headphone housings, speaker housings, soundproofing in walls or submarine engine rooms. However, the compositions of WO 2007/079230 are restricted to Bingham materials, which will not flow until stress can be applied and a certain value, the yield stress value, is reached. Beyond this point the flow rate increases steadily with increasing shear stress. In essence a particular minimum value has to be achieved to activate the material.

Thixotropic materials can be composed of a number of combinations, some of which are listed in this document and can be tailored to specific frequency and decibel adapted limits but all would be structured to suit biological protection from an early sound level stage while still allowing normal conversation and safety discussion to be maintained between co-workers when on-site. As well as this, immediate activation by pre-agitation or loud sound induction would make for a highly effective responsive invention.]

Dilitant materials are also known from the prior art as being used in hearing protection ear cups where external noise is prevented from passing directly through the ear cup itself (US 2003/0034198). Furthermore, the use of particles with mis-matched characteristic acoustic impedances embedded within a matrix of a material that can support shearing loads, propagates energy diffusion thereby providing acoustic and vibration damping (U.S. Pat. No. 5,400,296). However, dilitant materials become denser when exposed to high shear/mechanical forces such as energy waves. The denser the material, the easier it is to conduct the vibrations and hence the sound travels faster and more efficiently. This can be seen clearly in a simple dilitant material such as corn flour and water. When left in a container, it is liquid but attempt to stir it and it hardens up. If you go so far as to try and lift it out, it will go solid and as long as you continually move it between your hands, it will stay solid but the moment you leave it alone, it will return to liquid form and drip through your fingers. As such, dilitant materials are not effective sound absorbing materials due to the fact that they harden when exposed to energy waves.

A protective helmet comprising a rigid shell, an inner lining with at least one inflatable cell and inflation/deflation means is known from the prior art, as described in UK Patent Application No. GB 2 340 281. The inflatable cell may be filled with a fluid having thixotropic properties using a manual or electronic-powered pump. A method for obtaining rubber ear plugs is described in U.S. Pat. No. 3,782,379, where vulcanizable rubber is used at a certain viscosity to provide thixotropic properties.

There is a need therefore to provide inner and external ear protectors and/or inner- and outer-ear headphones which do not impact on the user's awareness of their surroundings while at the same time reducing or eliminating external ambient noise. The present invention intends to address at least one of the problems mentioned above.

SUMMARY OF THE INVENTION

The invention is based on the use of a thixotropic material as a sound absorbing medium in devices which are adapted to attach to or cover a user's ear. Examples of such devices would be noise protection headphones, audio headphones, and ear plugs. The thixotropic material has a resting viscosity which decreases as sound energy is incident on the material. As the viscosity of the material decreases, the level of attenuation of the incident sound increases. The thixotropic material reacts in such a way as to transfer some of the entering sound energy into kinetic energy that changes the structure of the thixotropic material and lessens the amount of sound energy passing through the material. Thus, when such a material is employed in noise protection headphones/earmuffs, the level of attenuation of sound will increase as the intensity of the sound increases, thereby allowing a user to hear low intensity sounds such as conversation though the headphones (when the material is at or close to a resting viscosity), while attenuating high intensity sounds.

Accordingly, in a first aspect, the invention provides a sound absorbing device of the type adapted to cover the ears of a user and comprising a sound absorbing material contained within a container in the form of a cellular scaffold, wherein the sound absorbing material comprises of a thixotropic material which is located in the cells of the cellular scaffold.

Ideally, the sound absorbing material may be enclosed within at least one container, and wherein the container may be expandable to allow an increase in volume of the sound absorbing material.

In one aspect of the invention, the cellular scaffold has a honeycomb structure typically having a plurality of cells arranged in a honeycomb structure, in which the thixotropic material is contained within the cells. Ideally, the cellular scaffold is in the form of a polymer film having cellular compartments or pockets, wherein the sound absorbing material is located within the cellular compartments.

Alternatively, the cellular scaffold may comprise at least one tube having first and second ends and a thixotropic material-containing lumen extending between the ends. Optionally, the tube may be disposed within the sound absorbing device such that at least one end of the tube faces towards incident sound. Typically, the cellular scaffold may comprise a plurality of tubes.

Ideally, the or each tube may be U-shaped and in which both ends of the tube preferably face towards incident sound. The or each tube may further comprise an additional tube disposed within the U-shaped tube between the first and second ends, wherein the additional tube has an open end which faces towards the incident sound.

In one embodiment of the present invention, one end of each of a plurality of tubes may be disposed within a base. In a further embodiment, the present invention may further comprise a plurality of substantially U-shaped tubes in which both ends of the tubes are disposed in the base.

In one embodiment of the present invention, at least two and preferably at least three (for example from 2 to 4 or 5 layers) layers of honeycomb structure may be arranged in a facing relationship, wherein the at least two layers are ideally disposed such that the cells of the honeycomb structure of a first layer are not in register with the cells of the honeycomb structure of the second layer. Preferably, the structure is made up of three layers oriented at 120° apart. The layers of honeycomb structure may be separated by a sound insulating layer. A sound insulating layer may be any sound insulating layer known to a person of ordinary skill in the art, such as a fluid, a gas, a polymer, and the like. The arrangement of the layers of honeycomb structure in this embodiment results in a Helmholtz resonance effect, that is, increasing sound absorption through differential air pressure between the out of register arrangement of the cells in each layer.

It should be understood that other embodiments of the cellular scaffold described herein can be arranged in layers and disposed relative to each other such that the cells of the cellular structure are not in register and separated by a sound insulating layer.

Ideally, the invention provides a sound absorbing device of the type adapted to cover the ears of a user and comprising a sound absorbing material, wherein the sound absorbing material comprises a thixotropic material.

The thixotropic material may be a fluid, a solid or semi-solid material such as a gel or resin. In a preferred embodiment of the invention, the thixotropic material is a liquid. Examples of thixotropic materials will be well known to those skilled in the field. Examples would include structured liquids, suspensions, emulsions, polymer solutions, aqueous iron oxide gels, vanadium pentoxide sols, starch pastes, pectin gels, flocculated paints, clays, soil suspensions, creams, drilling muds, flour doughs, flour suspensions, fibre greases, jellies, paints, honey, carbon-black suspensions, hydrophobically modified hydroxethyl cellulose, non-associative cellulose water solutions, flocculated polymer latex suspension, rubber solutions, metal slushes, bentonite clays, modified laponites, oils, lubricants, coal suspensions, xanthan gums, organic bentonite, fumed silica, aluminum stearate, metal soap, castor oil derivatives or thixotropic epoxy resin without prejudice or exclusion of like materials to these listed. The thixotropic material can be found to be effective in systems containing non-spherical particles, and is also associated with certain colloids which form gels when left to stand but become sols when stirred or shaken. They can also be associated with concentrated solutions of substances of high molecular weight colloidal suspensions.

Typically, the sound absorbing material consists essentially of a thixotropic material, especially a thixotropic liquid or gel.

In a flocculated system, the microstructure at rest can be seen to be a series of large floccules. A floccule is a small loosely aggregated mass of flocculent material suspended in or precipitated from a liquid. If an applied shear rate is given with an appropriate time interval, the floccule disintegrates into its constituent primary particles. The minimum viscosity can be seen with individual particles. Individual particles are considered to be those of simplest primary structure where the flocculated system has degraded to such a state as to contain the smallest possible particles within a specified shear range and without risking the integrity of the structure holding the material. In any flocculated system, the disintegration will be tending towards an equilibrium scenario that is held by hydrodynamic stresses pulling structures apart by erosion and upon removal of the applied stress/strain, that is, Brownian and shear forces rebuilding the structure by collision and accumulation of particles. In this flocculated structure the forces holding the structure together are colloidal in design and act over approximate distances of 10 nanometers, but may vary according to requirement.

Diffusion rates of isolated floccules decrease significantly as their respective size increases. There is a simple inverse relationship between particle size translational diffusion, which is demonstrated by Einstein's translational coefficient.

Shear thinning systems can occur due to loss of association in polymer solutions, rod-like alignment of particles in the direction of flow, microstructure rearrangement or flocculation disintegration.

Typically, the sound absorbing material is enclosed within a container, wherein the container is expandable to allow an increase in volume of the sound absorbing material. In a preferred embodiment of the invention, the sound absorbing device of the invention is constructed to allow shear be applied by a user to the thixotropic material contained therein, thereby activating the material by reducing its viscosity and increasing its sound absorbing capacity.

Ideally, the container comprises a cellular scaffold, and wherein the sound absorbing material is located in the cells of the cellular scaffold. Suitably, the cellular scaffold is formed of a thixotropic material.

Various types of containers are envisaged. Suitably, the container comprises a polymeric pouch which contains the sound absorbing material, wherein the polymeric pouch is expandable in response to pressure exerted by the thixotropic material as it decreases in viscosity and increases in volume. In another embodiment, the container comprises a tube having a first end, a second end, and a lumen extending between the first and second ends adapted for containing the thixotropic material, and wherein the tube is preferably disposed within the sound absorbing device such that at least one end of the tube faces towards incident sound (i.e. sound from the external environment). In a particularly preferred embodiment, a plurality of tubes are provided and ideally disposed in an interleaving arrangement. Thus incident sound enters each tube at one end and travels along the tube towards the second end. In another embodiment, the tube is curved, ideally u-shaped, in which case the tube is optionally disposed within the sound absorbing device such that both ends of the tube face towards incident sound, although the tube may be disposed such that both ends of the tube do not face towards incident sound, for example they could face away from incident sound. Ideally, a series of curved or U-shaped tubes are provided.

In this specification, the term cellular scaffold should be understood to mean a scaffold or substrate having a plurality of pockets or containers or compartments or tubes adapted to hold the thixotropic material. One example of a cellular scaffold would be a honeycomb structure, which may be formed using conventional moulding techniques from a polymeric or resin material. Another example of a cellular scaffold would be a polymer film having cellular compartments, wherein the sound absorbing material is located within the cellular compartments. Examples of such polymeric cellular scaffolds would be bubble wrap or polymer ice-cube making bags. In both cases, the thixotropic material would be disposed within the pockets of cells of polymer film. Another example of a cellular scaffold would be a series of tubes, suitably cylindrical tubes, and ideally U-shaped tubes.

Ideally, the thixotropic material is a material which exhibits a low viscosity drop in response to low intensity noise and disproportionately high viscosity decrease in response to high intensity noise. Examples of suitable materials include structured liquids, suspensions, emulsions, polymer solutions, aqueous iron oxide gels, vanadium pentoxide sols, starch pastes, pectin gels, flocculated paints, clays, soil suspensions, creams, drilling muds, flour doughs, flour suspensions, fibre greases, jellies, paints, honey, carbon-black suspensions, hydrophobically modified hydroxyethyl cellulose, non-associative cellulose water solutions, flocculated polymer latex suspension, rubber solutions, metal slushes, bentonite clays, modified laponites, oils, lubricants, coal suspensions, xanthan gums, organic bentonite, fumed silica, aluminum stearate, metal soap, castor oil derivatives or thixotropic epoxy resin. The use of a semi-liquid gaseous phase thixotropic combination which may tend towards gaseous state by agitation from the applied shear rate is also envisaged. This may also be achieved by partially evacuating the chamber in which it is disposed.

In a second aspect, the invention relates to a sound absorbing device according to the invention in the form of an ear plug, an audio headphone, an audio ear bud system, or a noise protection headphone.

Generally, in audio headphones and audio ear bud systems of the invention, the sound absorbing material is disposed between the speaker and the external environment, and within the ear buds, respectively. Thus, for example, the thixotropic material may form a barrier layer that is disposed in the headphone cup such that it covers the ear of a user, or is disposed within the ear buds to provide a barrier between the ear and the external environment. In this embodiment, the purpose of the thixotropic material is to dampen external sounds, thereby allowing a user to hear more clearly the sounds being produced by the speaker in the headphone/audio ear bud system.

Generally, for noise protection headphones, the sound absorbing material is disposed within the headphone to provide a barrier between the ear and the external environment.

Preferably, the cup of the headphone is a soft, deformable construction allowing a user to apply shear to the thixotropic material contained within the headphone.

Typically, an audio ear bud or ear plug of the invention is formed of a thixotropic material. Thus, the audio ear bud or ear plug may be formed of a moulded resinous thixotropic material. In another embodiment, the audio ear bud or ear plug may comprise an external shell and an internal cavity (container), wherein the thixotropic material is disposed within the cavity. The cavity may contain a container for holding the thixotropic material, for example a cellular scaffold as described above. Ideally, the ear plug or audio ear bud comprises a soft, deformable, material and allows the shear to be applied to the ear plug or audio ear bud by, for example, compressing or kneading the earplug or audio ear bud.

In a third aspect, the invention relates to a method of protecting the ears from high intensity noise comprising the step of placing a sound absorbing device of the invention over the ears, wherein the thixotropic material has a resting viscosity which exhibits low resistance to passage of low intensity noise, and wherein the thixotropic material decreases in viscosity in response to incident high noise to thereby exhibit high resistance to the high intensity noise.

In one embodiment of the invention, the method involves a step of applying shear to the thixotropic material in the sound absorbing device to increase the resistance to high intensity noise. In this way, for example, a user can control the noise resistance of the device. Thus, when a user of, for example, noise protection headphones is about to enter a noisy area of a processing plant, for example, they could remove the headphones and shake them to apply shear to the thixotropic material and thereby increase the noise protection, and then put the headphones on prior to entering the noisy area of the processing plant. Other methods of applying shear would be to, for example, massaging the thixotropic material. For audio ear buds or ear plugs of the invention, especially audio ear buds or ear plugs that are resiliently deformable, the ear bud or ear plug may be squeezed or kneaded to "activate" the thixotropic material. For headphones of the invention, the cups of the headphones may also comprise a construction which allows the thixotropic material contained therein to be squeezed or kneaded to activate the material.

The invention also relates to a sound absorbing material comprising a cellular scaffold in which the cells of the scaffold contain a thixotropic material. Typically, the cellular scaffold takes the form of a honeycomb structure in which the voids of the honeycomb structure contain a thixotropic material, ideally a thixotropic fluid. Thus, the sound absorbing material ideally comprises a layer of honeycomb structure having top and bottom seal layers which seal the voids in the honeycomb structure. In another embodiment, the cellular scaffold comprises a polymeric film having a multiplicity of cells, in which the cells contain the thixotropic material. This may take the form of a structure similar to layers of ice cube sheets interleaved or smaller dimensional rounded pockets that fit between each layer's cavity, i.e. one pocket would fit into the inner pocket space of another sheet and so on.

The honeycomb structure is seen as being potentially advantageous from a structural integrity and sound dampening combination allowing individual compartments but with the added advantage of strength and minimum non-thixotropic surface area.

The polymeric film in the form of a disc may be stacked one on top of the other. The discs may comprise a series of honeycomb structures, where each honeycomb structure may encase or may be comprised of a thixotropic material.

In a further embodiment of the invention, the thixotropic material may be selected to absorb sound energy at a specific frequency range. For example, the thixotropic matrix may comprise materials that respond maximally to the increasing noise levels at specific frequency ranges. In one embodiment, the thixotropic material provides hearing protection over a range of about 20 Hz to about 20000 Hz (20 KHz) of a human's hearing range. In another embodiment, the thixotropic material provides hearing protection for ultrasound (greater than 20 KHz) and infrasound (less than 20 Hz) as well as customised intermediate audible ranges for the purpose of particular environments such as rifle ranges, concerts, construction sites etc. For example in the area of ballistics in rifles and cannons, it is typically in the lower audible range of below 20 Hz but construction sites may be in the higher and lower ranges with high speed drills and low frequency pile drivers. Within the audible ranges, decibel is the main factor outside of the resonant range of 2 KHz to 4 KHz. There may be instances when infrasound/ultrasound can cause issues that are not audible to the human senses but can cause structural integrity problems. For example, in ultrasonic welding at frequencies from 20 KHz to 40 KHz, shielding may be required around the non targeted areas. In non-destructive testing of material flaws in ranges up to 10 MHz, again the non-desired target area may be shielded. There may also be issues surrounding animal welfare in ultrasound and infrasound environments. It is known to those skilled in the art as to the sensitivities of certain animals to ultrasound (bats, dogs, rodents, dolphins, whales, fish, cattle and horses etc).

Ultrasonic sound energy has potential physiological effects: it may cause an inflammatory response and the unwelcome heating effect of soft tissue. Ultrasound sound energy can also produces a mechanical rarefaction/compression wave through soft tissue. This pressure wave has the potential of causing microscopic bubbles in living tissues and can lead to the distortion of the cell membrane which affects intracellular activity. Ultrasound causes molecular friction and heats the tissues in the body. This effect is usually minor as normal tissue perfusion dissipates most of the heat, but with high enough intensity, it can create small pockets of gas in body fluids or tissues which may expand and contract. This phenomenon can be called cavitation. It may be seen then that a need for thixotropic energy absorbance could be utilised in medical environments for shielding either from diagnostic, medical, surgical or dentistry purposes. In each of these cases narrow ranges may be isolated to allow for specific shielding for specific purposes. For example, when utilising ultrasonic surgery in the regions of 250 KHz to 2 MHz, only the desired body area should be exposed to the full strength of energy so as to lower the hazards attached to the non-affected part.

In the case of most high noise risks, the frequency range is quite low and could be simple to have one thixotropic material. It may require a second thixotropic material which deal with higher frequency noises such as high speed drills or alarms.

In one embodiment of the invention, the thixotropic material may be selected from the group comprising structured liquids, suspensions, emulsions, polymer solutions, aqueous iron oxide gels, vanadium pentoxide sols, starch pastes, pectin gels, flocculated paints, clays, soil suspensions, creams, drilling muds, flour doughs, flour suspensions, fibre greases, jellies, paints, honey, carbon-black suspensions, hydrophobically modified hydroxethyl cellulose, non-associative cellulose water solutions, flocculated polymer latex suspension, rubber solutions, metal slushes, bentonite clays, modified laponites, oils, lubricants, coal suspensions, xanthan gums, organic bentonite, fumed silica, aluminum stearate, metal soap, castor oil derivatives or thixotropic epoxy resin. The thixotropic material may be used as a sound absorbing material for the following applications:

1) Filling for ear plugs;
2) Interior of ear muff whether as a single layer, multiple layers or a tubular structure;
3) Outer interface for a noise cancelling headphone set or audio ear bud system to lessen ambient noise to user; and
4) Interior of an ear band whether as a single layer, multiple layers or tubular structure.

The advantages of such a system are:

1) No electronics or power sources are required;
2) The at least one thixotropic layer will respond proportionately to the amount of sound energy entering, so as to allow the user to hear voices or warnings but further dampen any extremely loud noises, for example, machinery such as drills, pile drivers, guns, house alarms, trains, and the like.
3) The material is cheap to produce and manufacture into existing headphone/ear muff/ear plug designs.
4) The response rate of the material will not require a yield stress rate such as that required for Bingham fluids, and hence will work quicker and be able to be pre-agitated before entering the environment.
5) The main difference between linear viscoelasticity and thixotropy are that the former remains unchanged due to elasticity in the linear region and the latter breaks down in structure, even though both materials are time dependent.

Thus, the sound absorbing device of the present invention differs from conventional sound absorbing devices in that it is particularly concerned with thixotropic materials which attribute a decrease of the apparent viscosity under constant shear stress or shear rate, immediately followed by a gradual return to equilibrium once the shear stress or strain is removed. It is dependent on the finite time taken for the shear induced structural change in the thixotropic material microstructure caused by the stress tearing and flow induced collisions. Once flow ceases, Brownian motion can return the elements of the microstructure back to a more favourable equilibrium once again. It is a reversible process determined by time and shear stress or strain.

In terms of preventing hearing damage, time is as important a concern as amplitude. The human hearing system is able to deal with particular frequency and amplitude combinations for finite periods of time. Since thixotropic compositions act immediately and progress in lowering viscosity as time passes under shear rate, the protection is increased for the user the longer they remain in a high-risk sound environment. This allows for the use of this invention in ear plugs designed for concert audiences who wish to hear the music or performance but at increasingly safe limits as well as all other listed uses for construction workers, security personnel, dog handlers, dentists, firearms users, military personnel and associated sound induced trauma risk environments.

The thixotropic material can be comprised of a variety of materials, comprising existing thixotropic liquids and resins or a combination thereof structured liquids, suspensions, emulsions, polymer solutions, aqueous iron oxide gels, vanadium pentoxide sols, starch pastes, pectin gels, flocculated paints, clays, soil suspensions, creams, drilling muds, flour doughs, flour suspensions, fibre greases, jellies, paints, honey, carbon-black suspensions, hydrophobically modified hydroxethyl cellulose, non-associative cellulose water solutions, flocculated polymer latex suspension, rubber solutions, metal slushes, bentonite clays, modified laponites, oils, lubricants, coal suspensions, xanthan gums, organic bentonite, fumed silica, aluminum stearate, metal soap, castor oil derivatives or thixotropic epoxy resin. The particular concentrations have yet to be determined but may comprise pre-existing sound insulation resins or solutions or newly tailored mixtures. The thixotropic material may be injected into a cavity in earplugs and/or ear muffs.

The louder the sound input the thixotropic material becomes less dense and resists conducting the sound to the ear. In addition to this, what remaining sound is left will find it harder to pass through a now significantly less dense material. But if the sound is very quiet, it will allow it to pass. This then creates a set of hearing protection ear muffs that allow conversation but instantly react to loud noises of varying frequencies and levels as soon as they try and enter the ear.

The inclusion of a harder thixotropic material in a cavity for ear muffs or headphones would also be easier than trying to inject a dilitant material in less viscous form. An expansion area in the cavity would allow the material to change state successfully and not rupture or pressurise the cavity so as to restrict change. Such an application could be used in noise cancelling headphones so as to further restrict external noise and allow the user to listen to their music at lower volumes than previously experienced.

DEFINITIONS

It is to be taken in this specification that the term "thixotropic material" refers to a material that has a certain viscosity in a resting state, but which changes viscosity in response to shear. Thixotropic material may take the form of solids, liquids, gases, and semi-solid materials. Examples of thixotropic materials include structured liquids, suspensions, emulsions, polymer solutions, aqueous iron oxide gels, vanadium pentoxide sols, starch pastes, pectin gels, flocculated paints, clays, soil suspensions, creams, drilling muds, flour doughs, flour suspensions, fibre greases, jellies, paints, honey, carbon-black suspensions, hydrophobically modified hydroxethyl cellulose, non-associative cellulose water solutions, flocculated polymer latex suspension, rubber solutions, metal slushes, bentonite clays, modified laponites, oils, lubricants, coal suspensions, xanthan gums, organic bentonite, fumed silica, aluminum stearate, metal soap, castor oil derivatives or thixotropic epoxy resin. The term should be taken to include thixotropic materials which show a time-dependent change in viscosity, i.e. the longer the fluid/material undergoes shear stress, the lower its viscosity. Many gels and colloids are thixotropic materials which exhibit a stable form at rest but become fluid when agitated. Typically the thixotropic material has a dynamic viscosity of from $10^{-3}$ to $10^3$ Pa/s, preferably $10^{-2}$ to $10^2$ Pa/s, and ideally 2 Pa/s to 250 Pa/s, when measured using a Rotating Cylinder Viscometer method (European Pharmacopoeia 5.0 2.2.10 (January 2005)). For example, if a liquid (or solid, gas and semi-solid material) is placed in viscometer and a solid object, such as a polyamide rotor, is immersed in the liquid and rotated at a constant speed around its central axis, the rotor will experience a retarding force due to the viscous drag of the liquid. By knowing the dimensions of the viscometer, the viscosity of the liquid can be calculated. The viscosity of non-Newtonian systems may also be measured using a Rotating Cylinder Viscometer by obtaining two shear rates and interpolating the readings. In a preferred embodiment, the thixotropic material has a viscosity in the range of honey (preferably Boyne Valley Honey (Ireland)) and peanut butter (preferably Panda smooth peanut butter (Boyne Valley Group, Ireland)).

The cellular scaffold of the present invention, or part thereof, for example the part of the scaffold which holds the tubes, or indeed the tubes themselves, may be composed of, for example, Sheetrock, Mass Loaded Vinyl, Hardwood, rubber, cork, fibreboard, wood wool cement, glass silk, mineral wool, acoustic foam, sponge, acoustic tile, glass fibre, porous plastic, porous rubber, rubber foam, melamine sponge, foam, rubber, latex, porous absorbers, and aerated plaster. It should also be taken in this specification that the cellular scaffold may be composed of a thixotropic material described above.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

BRIEF DESCRIPTION OF THE DRAWINGS

The invention will be more clearly understood from the following description of an embodiment thereof, given by way of example only, with reference to the accompanying drawings, in which:

FIG. 10A-10D illustrates in more detail the substantially U-shaped structure of FIG. 7 in (A) front, (B) plan, (C) perspective and (D) side views;

DETAILED DESCRIPTION OF THE DRAWINGS

The invention is based on the use of a thixotropic material as a sound absorbing medium in devices which are adapted to attach or cover a user's ear. Examples of such devices would be noise protection headphones, audio headphones, and ear plugs. The thixotropic material has a resting viscosity which decreases as sound energy is incident on the material. As the viscosity of the material decreases, the level of attenuation of the incident sound increases. Thus, when such a material is employed in noise protection headphones/earmuffs, the level of attenuation of sound will increase as the intensity of the sound increases, thereby allowing a user to hear low intensity sounds such as conversation though the headphones (when the material is at or close to a resting viscosity), while attenuating high intensity sounds.

Figure 1:
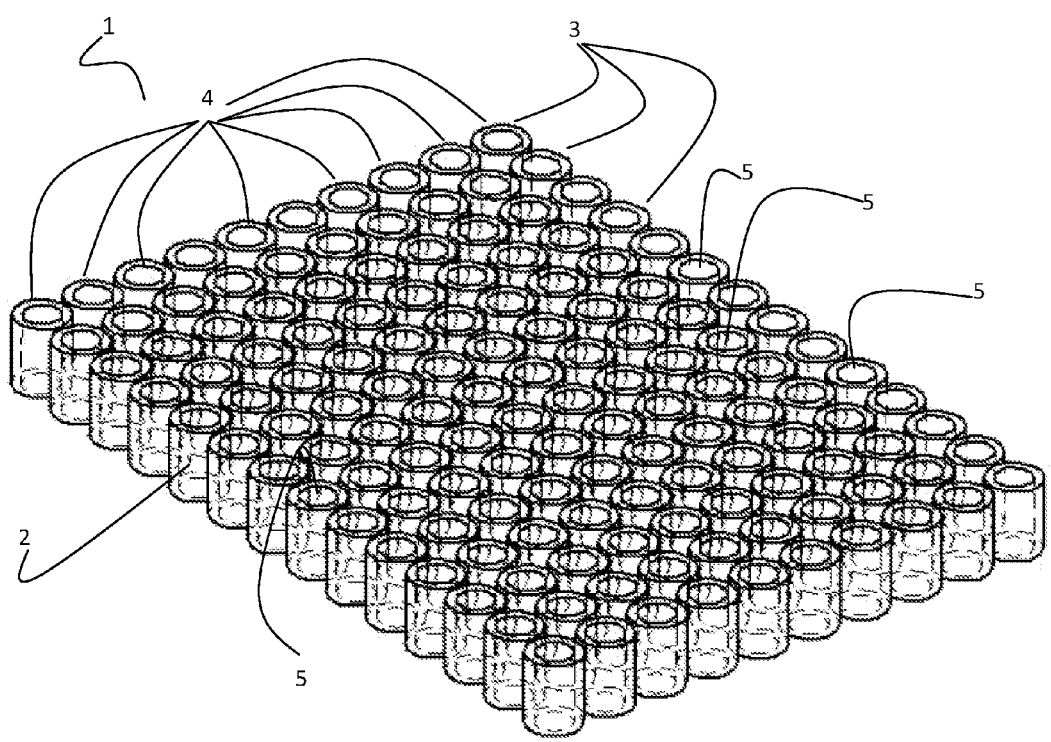
FIG. 1 illustrates a first honeycomb layer structure for a sound absorbing device of the present invention.

Referring now to the figures, where FIG. 1 illustrates a general embodiment of a sound absorbing device of the present invention. Specifically, FIG. 1 illustrates a perspective view of a sound absorbing device of the present invention, which in this instance is configured as a honeycomb layer and is generally referred to by reference numeral 1. The honeycomb layer 1 is arranged in a sheet 2 and is formed from polyethylene plastic foil. The sheet 2 comprises a series of rows 3 and columns 4 of a honeycomb structure or cells 5. The cells 5 are filled with a thixotropic material, in this case lubricating oil. The thixotropic material reacts in such a way as to transfer some of the entering sound energy into kinetic energy that changes the structure of the thixotropic material and lessens the amount of sound energy passing through the material. In a further embodiment, the honeycomb cells 5 are comprised of the thixotropic material. The honeycomb structure may be constructed from rigid or pliable integrity material depending on tailored use. It is seen that an expansion ability will be required in some embodiments so as pressure will not increase with phase change.

Figure 2:
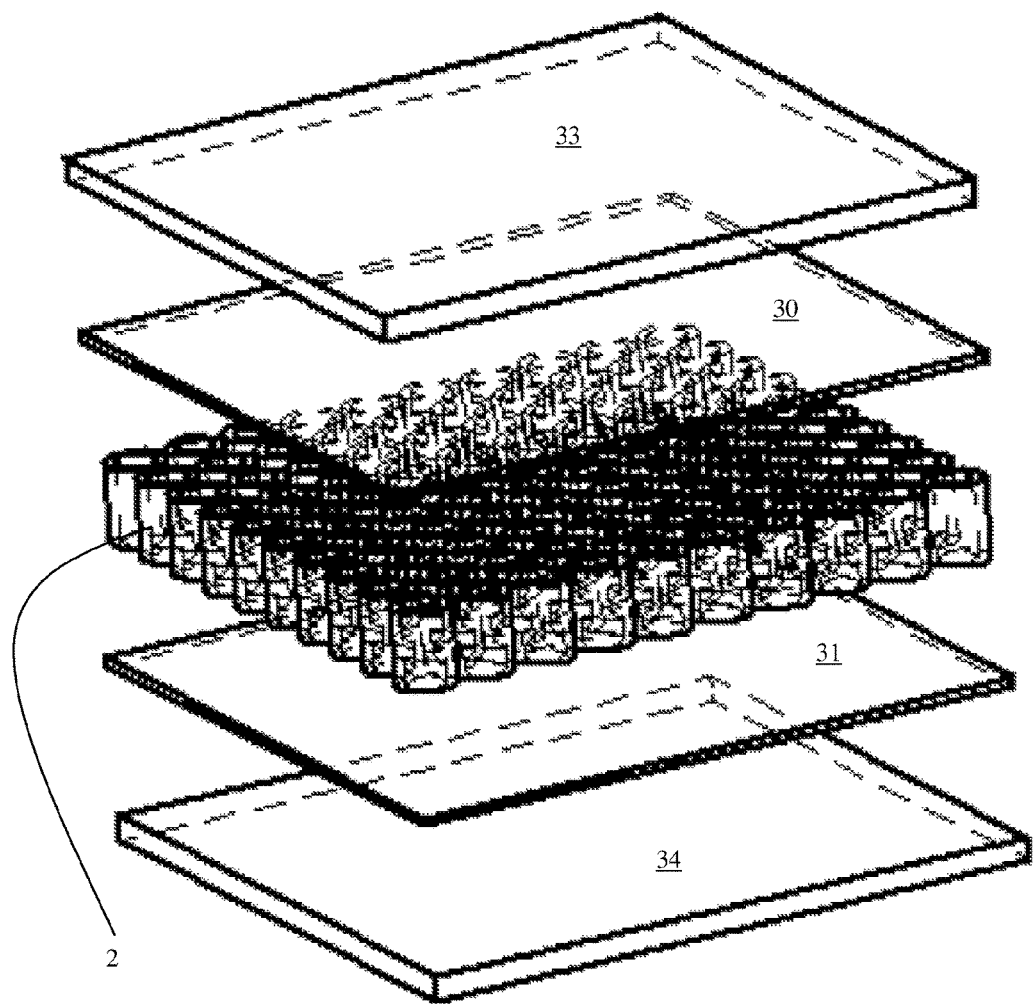
FIG. 2 is an exploded view of a thixotropic device of the present invention comprising a honeycomb lattice as illustrated in FIG. 1.

In FIG. 2 there is illustrated a sound absorbing device 1 of FIG. 1 sandwiched between a series of layers of material. The sound absorbing device 1 of FIG. 2 comprises the sheet 2 of thixotropic material formed from thixotropic epoxy resin which is known to those skilled in the art in sound-proofing and structural sealants for building construction sandwiched between adhesive seal layers 30,31. The outer adhesive seal layers 30,31 seal the voids of the cells 5 of the honeycomb structure. An outer layer 33 and inner layer 34 are placed on the side of the adhesive seals 30,31 facing away from the sheet 2. The combination of the sheet 2 and layers 30,31,33,34 provide a sound absorbing device 1 of the present invention.

Figure 3:
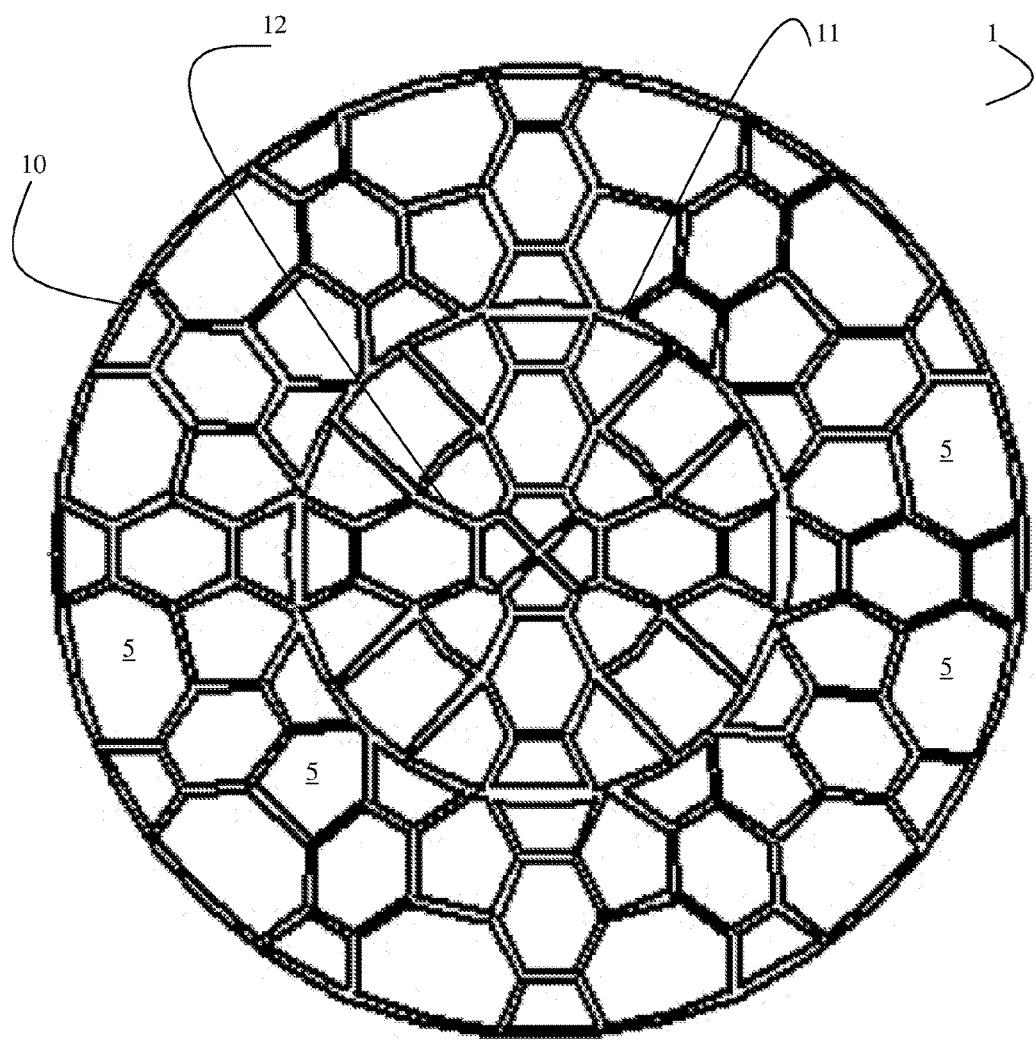
FIG. 3 illustrates a second honeycomb layer structure for a sound absorbing device of the present invention.
Figure 4:
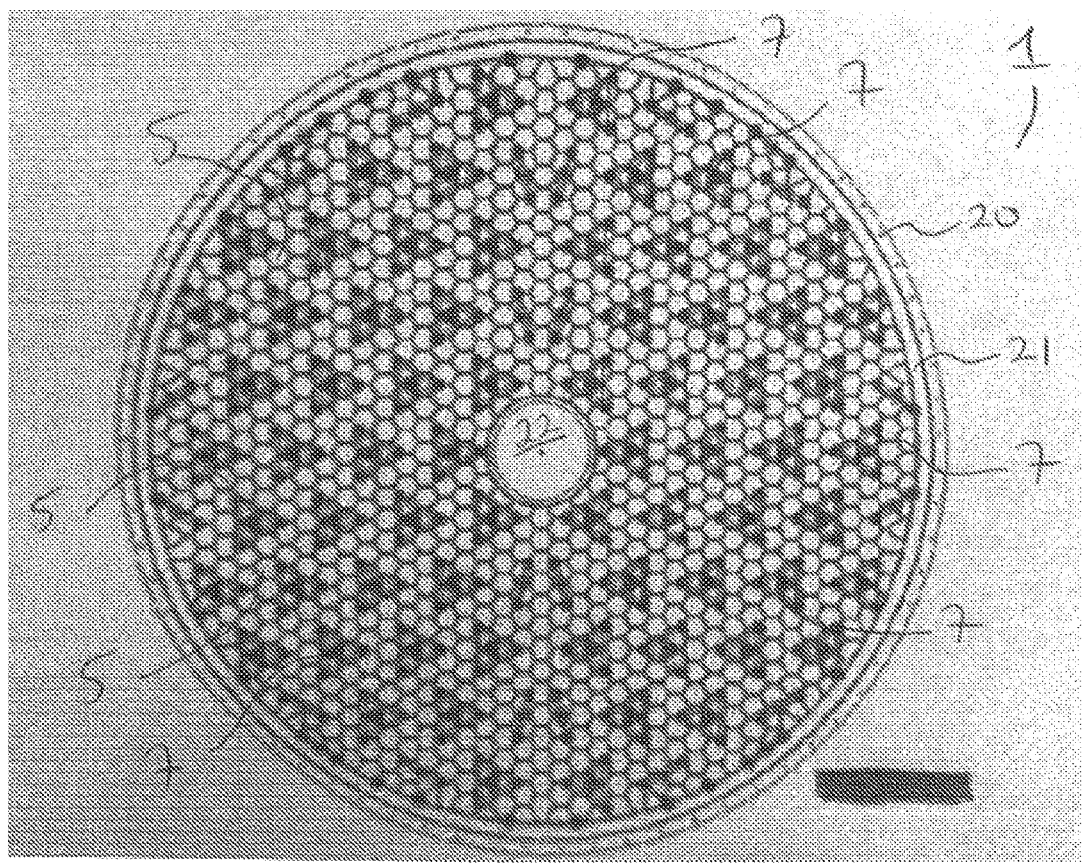
FIG. 4 illustrates a third honeycomb layer structure for a sound absorbing device of the present invention.
Figure 9:
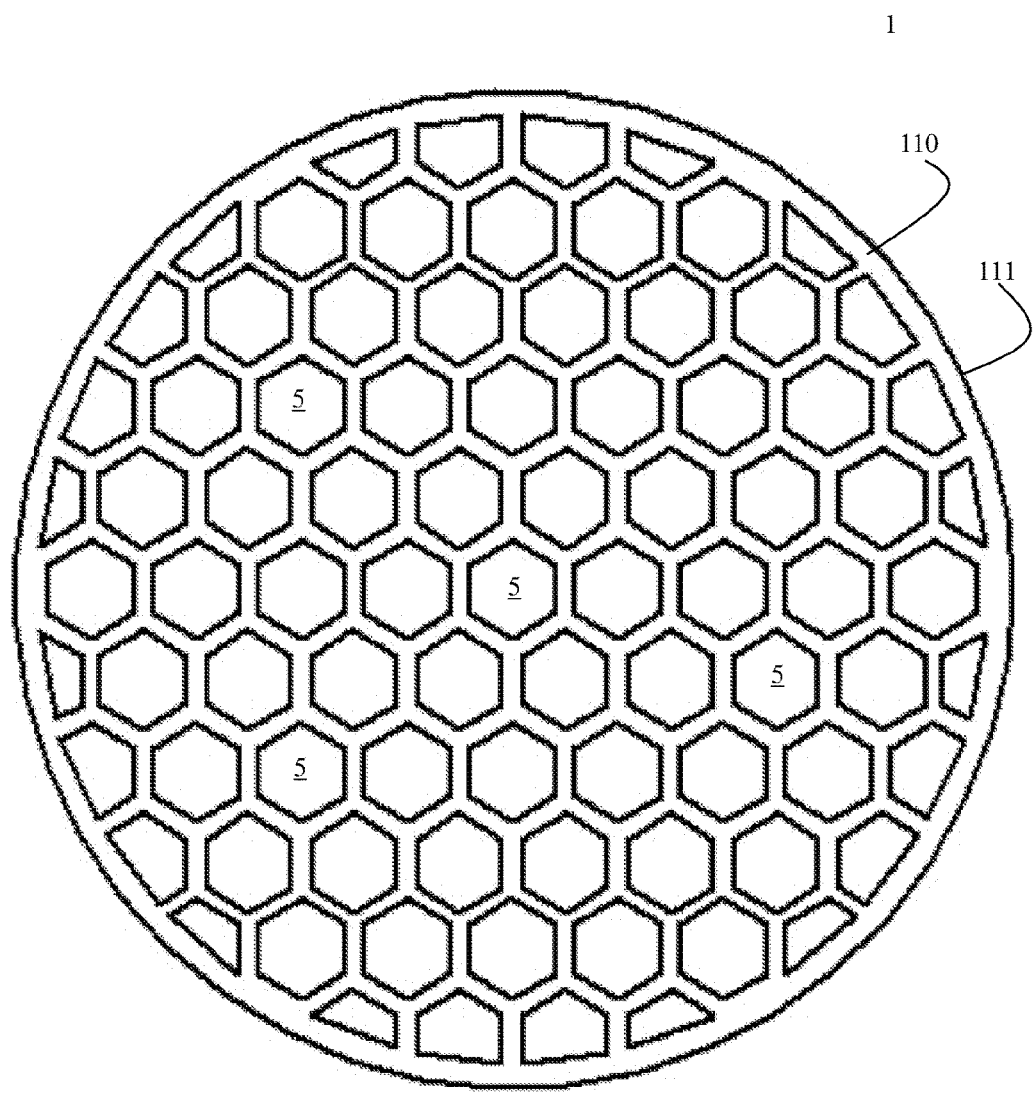
FIG. 9 illustrates a fourth honeycomb layer structure for a sound absorbing device of the present invention.
Figure 10C:
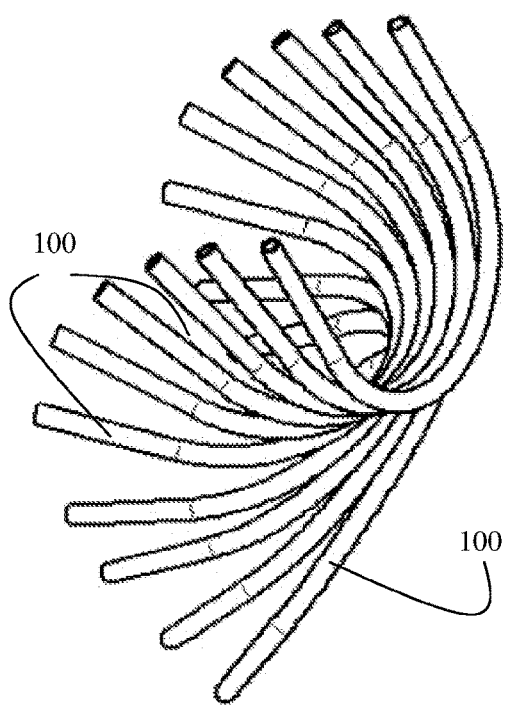
Figure 10D:
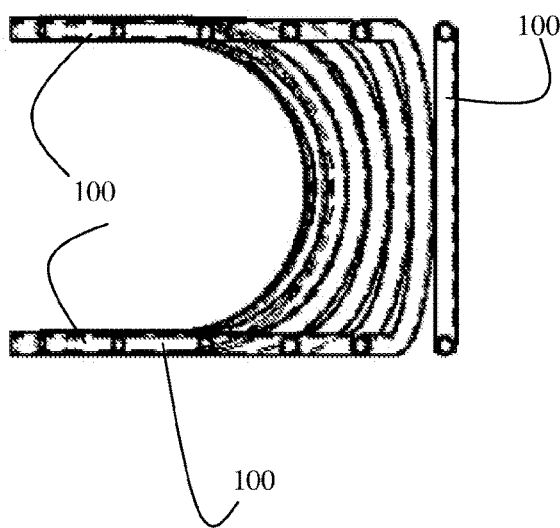
Figure 11:
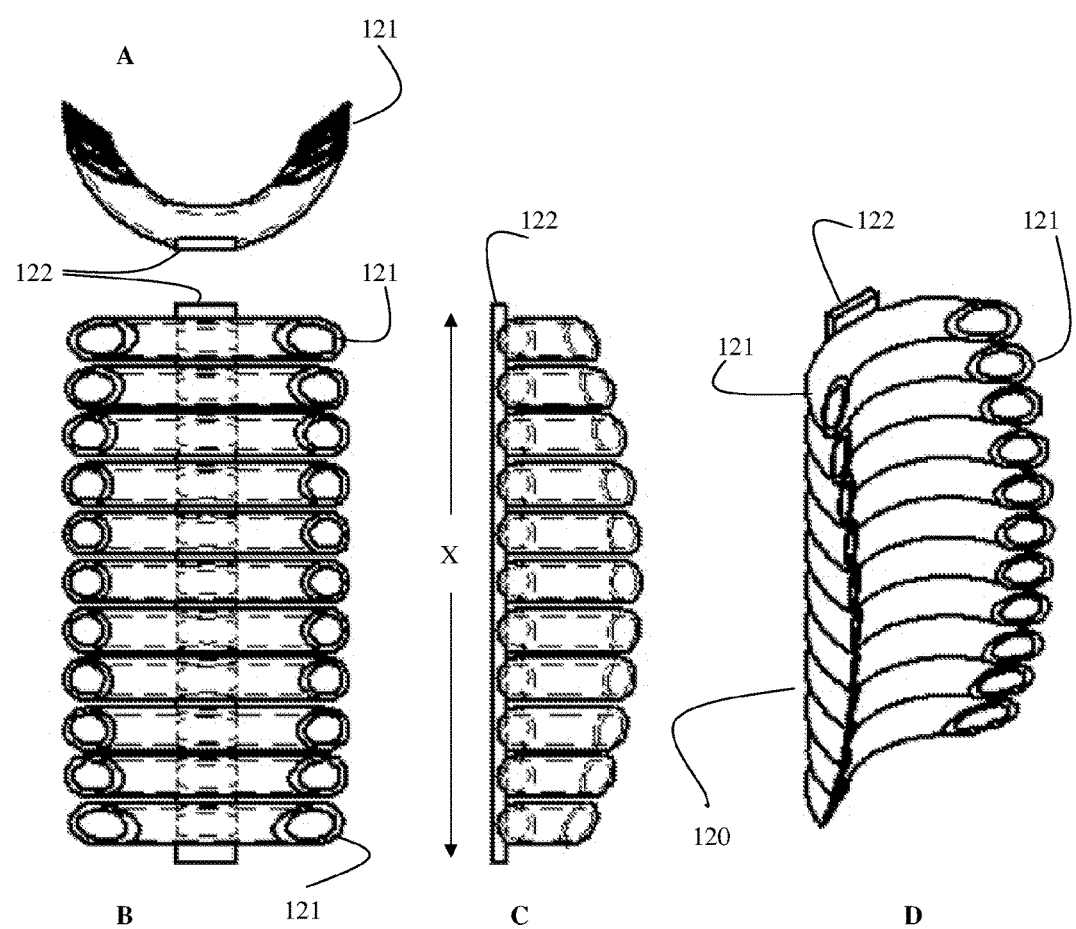
FIG. 11A-11D illustrates a second substantially U-shaped structure for a sound absorbing device of the present invention in (A) plan, (B) front, (C) side and (D) perspective views.
Figure 12:
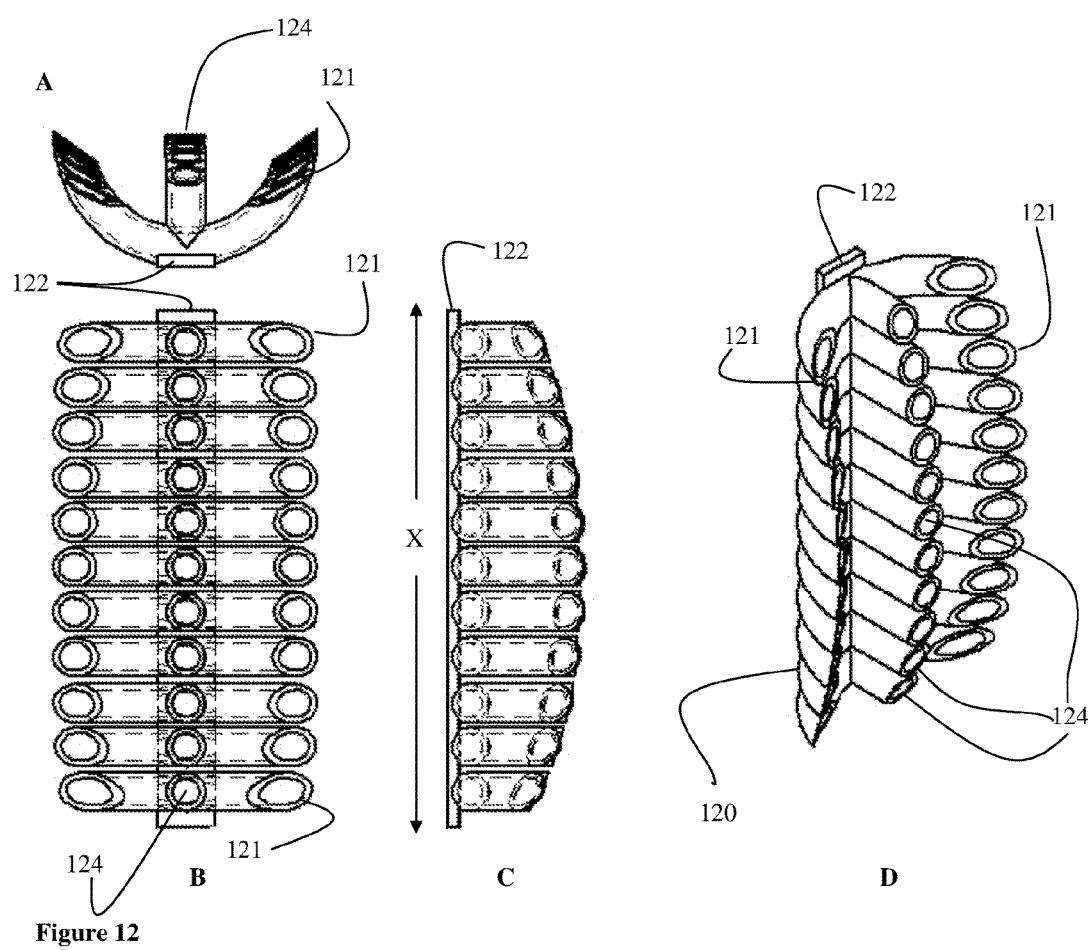
FIG. 12 illustrates a third substantially U-shaped structure for a sound absorbing device of the present invention in (A) plan, (B) front, (C) side and (D) perspective views.
Figure 13:
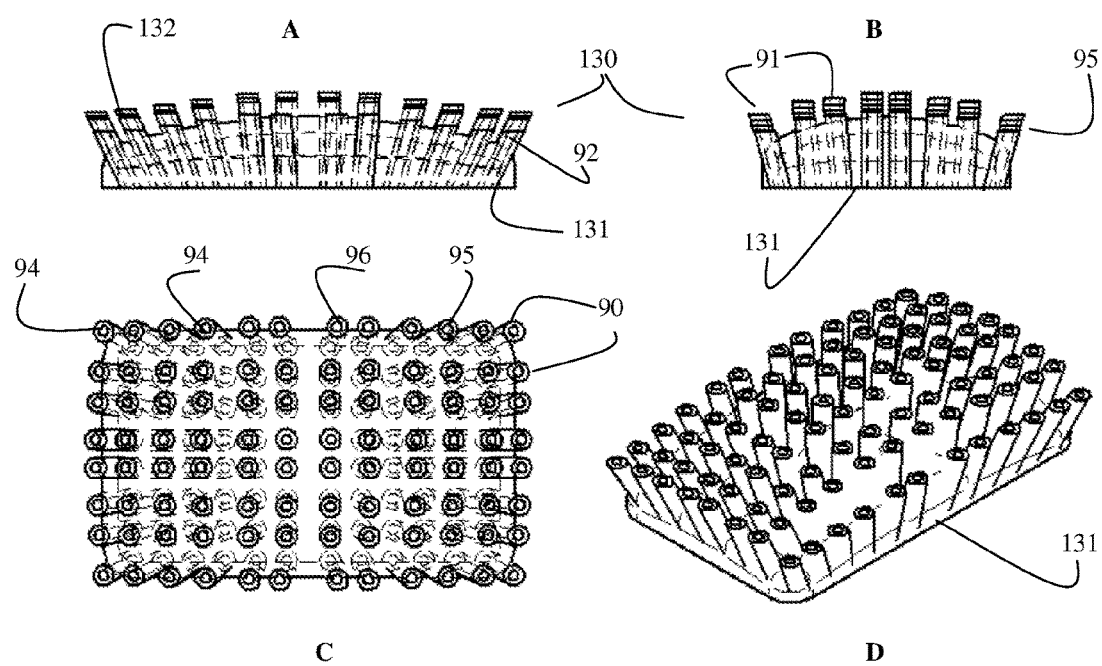
FIG. 13 illustrates a multiple cylindrical tubular structure for a sound absorbing device of the present invention in (A) side, (B) elevation, (C) plan and (D) perspective views.

In FIG. 3 there is illustrated a further embodiment of the present invention where the device 1 is represented by a polymeric film having a multiplicity of honeycomb cells 5 and configured as a series of discs 10,11,12. The series of discs 10,11,12 are stacked one on top of the other with decreasing diameters to provide a conical or substantially conical shape. An outer disc 10 has a diameter larger than inner disc 11, which has a diameter larger than disc 12 when the central radius point is taken at the centre of the device 1. FIG. 4 illustrates a further embodiment of the device 1 of FIG. 3. An outer disc 20 and 21 comprise a non-thixotropic material. The honeycomb structure may be constructed from rigid or pliable integrity material depending on tailored use. It is seen that an expansion ability will be required in some embodiments so as pressure will not increase with phase change. The inner disc 22 may aid in this expansion as well as the outer circumference material 21. The outer disc 20 is rigid so as to aid manufacturing process and disposal within a housing. Between outer disc 21 and an inner disc 22 is found a collection of honeycomb cells 5. The honeycomb cells 5 are interspersed with thixotropic material-filled structures 7. In the illustrated embodiment, the honeycomb cells 5 are composed of a thixotropic material. FIG. 9 illustrates a further embodiment of the device 1 of FIG. 3. A disc 110 comprises a non-thixotropic material and having an outer rim 111. The honeycomb structure may be constructed from rigid or pliable integrity material depending on tailored use. The outer rim 111 is rigid so as to aid manufacturing process and disposal within a housing. Within the outer rim 111 is found a collection of honeycomb cells 5. The honeycomb cells 5 may be filled with thixotropic material. In the illustrated embodiment, the honeycomb cells 5 are composed of a thixotropic material.

Figure 5:
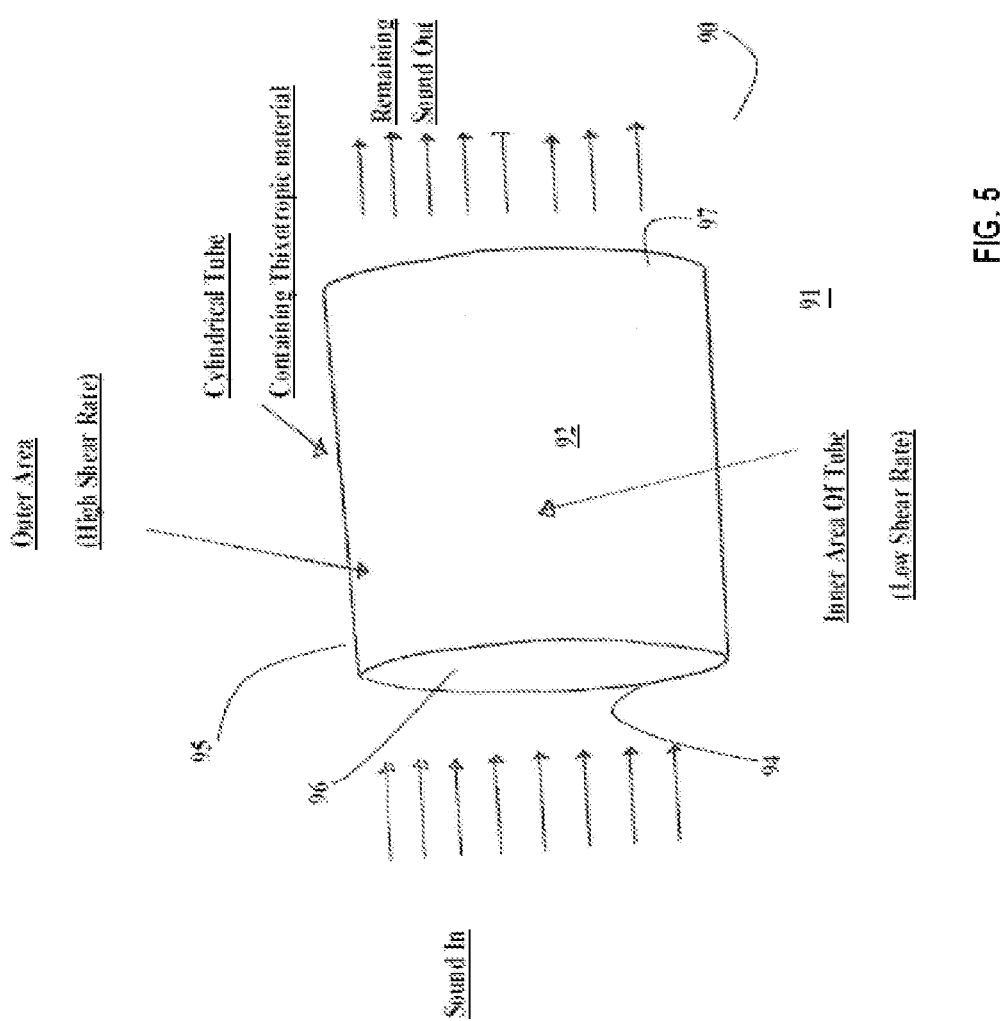
FIG. 5 illustrates a cylindrical tubular structure for a sound absorbing device of the present invention.

Referring to FIG. 5, these is illustrated a cellular scaffold forming part of a sound absorbing device according to an alternative embodiment of the invention. The cellular scaffold 90 comprises a cylindrical tube 91 having an exterior surface 92 and an interior surface 94 defining a lumen 96 which is filled with a thixotropic material. In use, the cylindrical tube would be arranged within the sound absorbing device (not shown) such that external sound would enter the tube at a first end 95 and travel through the tube to a second end 97. In doing so, the sound would cause some movement of the thixotropic material within the tube. The material at the walls of the tube would experience friction and be exposed to a higher shear rate than the material at the centre of the tube. Thus, the thixotropic material adjacent the walls of the tube would have greater sound absorbing capacity compared to the material at the centre of the tube.

Figure 6:
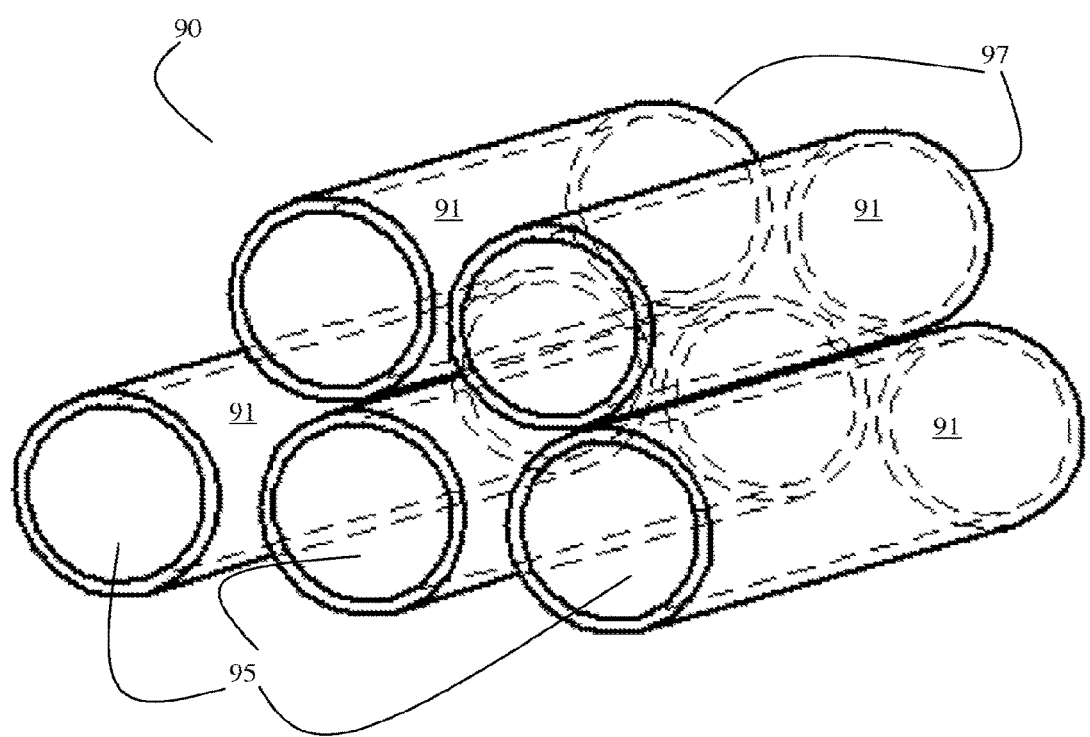
FIG. 6 illustrates a multiple interleaved cylindrical tubular structure for a sound absorbing device of the present invention.

Referring to FIG. 6, these is illustrated an alternative cellular scaffold forming part of a sound absorbing device of the invention. The cellular scaffold 90 comprises a series of cylindrical tubes 91 arranged in an interleaving arrangement. In use, the cylindrical tubes would preferably be arranged within the sound absorbing device (not shown) such that external sound would enter the tube at a first end 95 and travel through the tube to a second end 97.

Referring to FIG. 7 and FIGS. 10A-10D, there is illustrated a series of thixotropic material-containing cylindrical tubes 100, each tube being coiled back on itself, the series of curved tubes forming a U-shaped structure 101. Each tube has two ends which, due to the U-shape, face the same direction. In use, the U-shaped structure is disposed within a sound absorbing device such that the ends of the tube face towards incident sound, and the bend on the U-shaped structure is disposed towards the user's ear. This structure directs the incoming sound back out to the environment. As such, most of the sound energy would be directed back out to the environment even though the transmission percentage of sound in this part of the device 1 would be quite low given that the sound energy passes through thixotropic material.

The housing 90 and substantially U-shaped structure 100 may be immersed in thixotropic material to further dampen and attenuate any sound not passing through the tubes.

Figure 8:
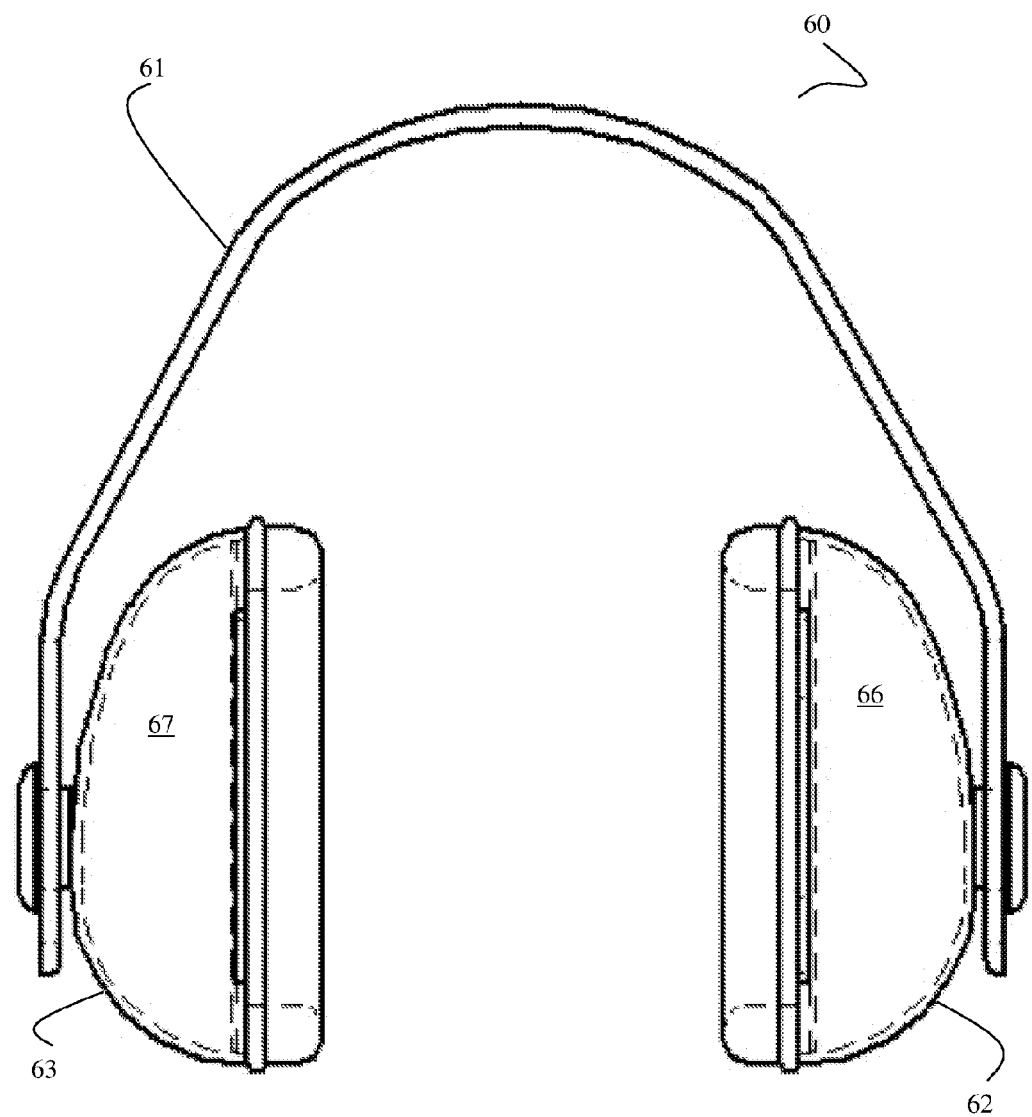
FIG. 8 illustrates a set of headphones comprising a sound absorbing material enclosed in a container of the present invention.

Referring to FIG. 8, there is illustrated a sound absorbing device according to the invention, in the form of a headphone set 60, and comprising a headband 61 connecting ear coverings 62, 63 together. Each ear covering 62, 63 includes a thixotropic material in the form of a polymeric sheet comprising a multiplicity of cellular pockets, wherein the thixotropic material is located within the cellular pockets (not shown).

When a user is listening to music on the headphones 60, thixotropic material located within the cellular pockets of the polymeric sheet within the cavities 66, 67 allows low intensity sounds like voices to be heard, while high intensity sounds like those from a pneumatic drill or jet engine reduced. As such, the user does not need to increase the volume of the music to obviate the interfering external sounds. This advantage of the sound absorbing device 1 of the invention reduces the damage done to the hearing while maintaining the enjoyment of the music being listened to.

Figure 7:
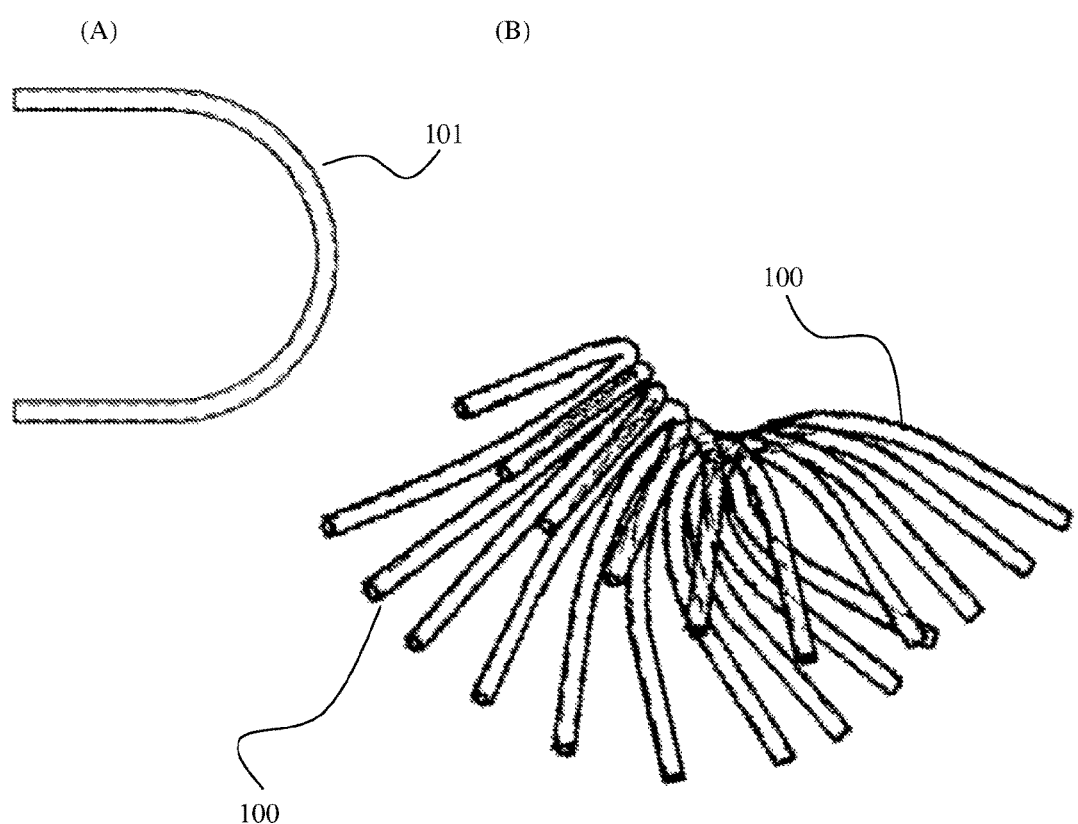
FIG. 7 illustrates (A) a side view and (B) a perspective view of a substantially U-shaped structure for a sound absorbing device of the present invention.
Figure 14:
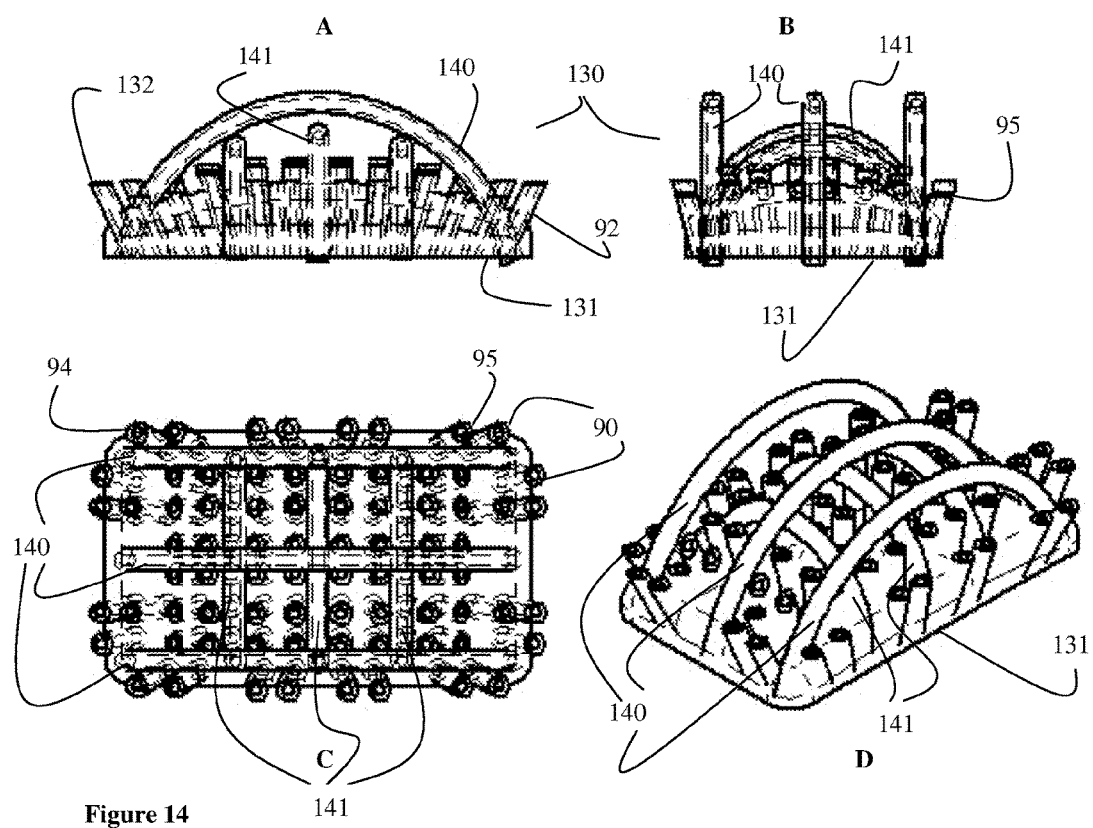
FIG. 14 illustrates a second multiple cylindrical tubular structure for a sound absorbing device of the present invention (A) side, (B) elevation, (C) plan and (D) perspective views.

Referring to FIGS. 11A-11C and FIGS. 12A-12D, there is illustrated a further embodiment of cellular scaffold of the invention including the series of thixotropic material-containing cylindrical tubes 100 previously described with reference to FIG. 7 and FIG. 10. In the illustrated embodiments, each tube 121 is also coiled back on itself, the series of curved tubes 121 forming a substantially U-shaped structure 120. Each tube has two ends which, due to the U-shape, face the same direction. The series of substantially U-shaped structures 121 are connected to and supported by a spine 122. The spine may be flexible or rigid. The tubes 121 are connected to the spine 122 such that the tubes 121 point away from a plane X of the spine 122. As illustrated in FIG. 12A-12D, an additional series of cylindrical tubes 124 are connected to and in fluid communication with the curved tubes 121. The cylindrical tubes 124 lie perpendicular to the plane X of the spine 122. In FIGS. 13A-13D there is illustrated a further embodiment of a cellular scaffold 130 forming part of a sound absorbing device of the present invention. The cellular scaffold 130 comprises a plurality of tubes 90, as illustrated in FIG. 5, embedded in a base 131. The appearance of the scaffold 130 can be described as being like a "hedgehog". As per FIG. 5, the plurality of tubes 90 comprises a cylindrical tube 91 having an exterior surface 92 and an interior surface 94 defining a lumen 96 which is filled with a thixotropic material. In use, the cylindrical tube would be arranged within the sound absorbing device (not shown) such that external sound would enter the tube at a first end 95 and travel through the tube to a second end embedded in the base 131. In doing so, the sound would cause some movement of the thixotropic material within the tube. The material at the walls of the tube would experience friction and be exposed to a higher shear rate than the material at the centre of the tube. Thus, the thixotropic material adjacent the walls of the tube would have greater sound absorbing capacity compared to the material at the centre of the tube. FIG. 14 illustrates a further embodiment of the cellular scaffold 130 of FIG. 13. A second end 97 of the cylindrical tube 91 is exposed by an open-ended base 132. A series of substantially U-shaped cylinders 140 are embedded in the base 131, crossing from side 133 to the opposite side 134 of the base 131. A further series of substantially U-shaped cylinders 141 are embedded in the base 131, crossing from side 135 to the opposite side 136 of the base 131, and positioned such that the cylinders 141 are lying beneath cylinders 140.

Materials and Testing Method

Figure 20:
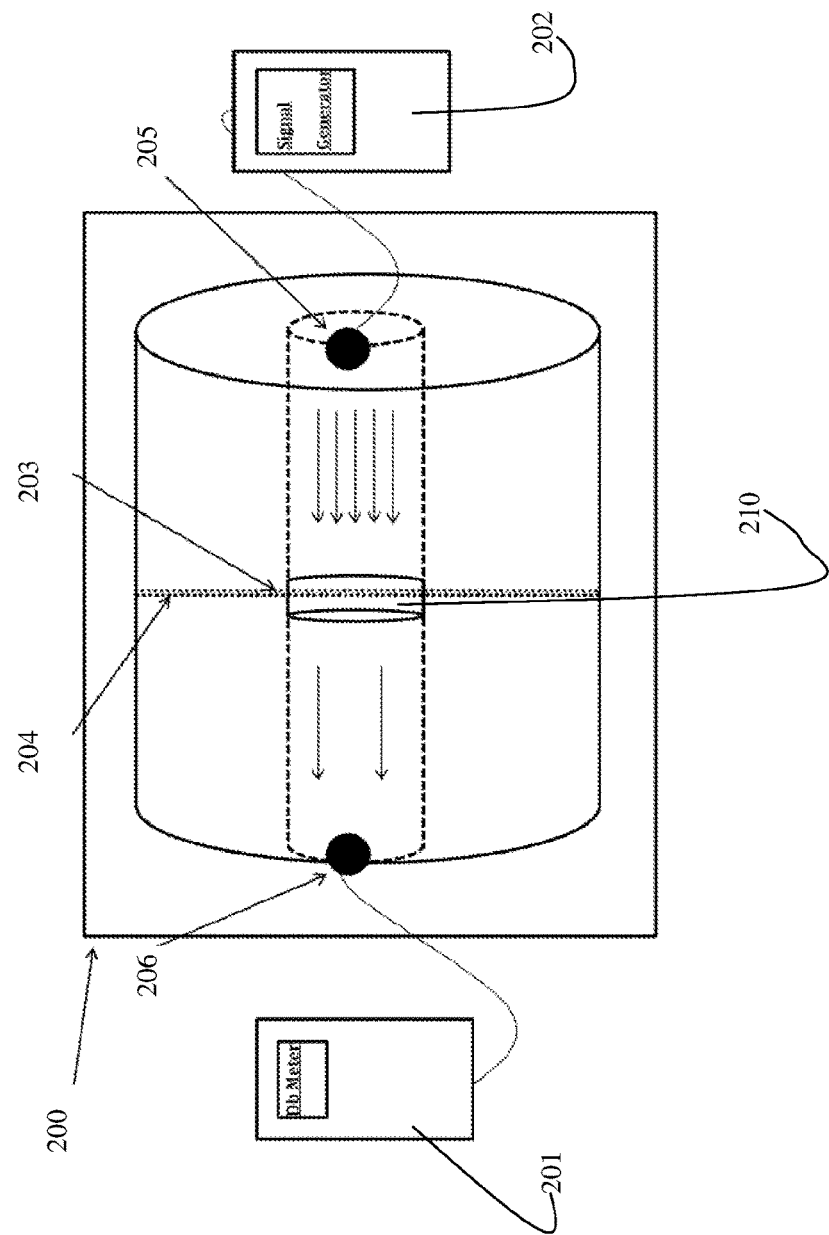
FIG. 20 is a schematic diagram of the testing environment used to determine the dB Change vs. Frequency (Hz) as shown in FIGS. 15 to 19.

A testing environment to ascertain the sound absorbing properties of the present invention is illustrated in FIG. 20. The testing environment comprises an anechoic chamber 200 with a decibel (dB) meter 201 on one side of the chamber and a signal generator 202 on the other side of the chamber. A hearing protector 203, for example a pair of headphones, is placed in the chamber 200 between the dB meter 201 and the signal generator 202. The hearing protector 203 is constructed such that there is a join 204 running down the middle of the protector to accommodate the easy insertion and removal of a cellular scaffold 210 (with reference to any of the cellular scaffolds of the Drawings and Description) of the present invention inside the hearing protector 203. A cellular scaffold of the present invention is placed within the protector 203 between the dB meter 201 and the signal generator 202 within the chamber 200. A small speaker 205 is attached to the signal generator 202 and placed between the signal generator 202 and the cellular scaffold of the present invention. A sound sensor 206 (a Digitech QM 1592 class 2 professional sound level meter) is attached to the dB meter 201 and placed between the dB meter 201 and the cellular scaffold of the present invention.

A measurement for background/ambient noise was first measured to ensure that all sound from the signal generator 202 was being received by the dB meter sound sensor 206. The control used for the experiments is the industry standard headphone ear protectors manufactured by 3M®, model type 1430C. The sound absorbing material of the control headphones were tested at frequencies indicated by the manufacturer, namely 125, 250, 500, 1000, 2000, 4000 and 8000 dB. A reading for each frequency was measured in triplicate and an average reading was calculated. The reduction in the dB level achieved by the sound absorbing material at each frequency was calculated by subtracting the measured dB level from the dB level measured when no sound absorbing material was present.

Results

The embodiments described in FIGS. 1, 3, 11, 13 and 14 were tested. The embodiments were assigned P1 (FIG. 11), P2 (FIG. 3), P4 (FIG. 13), P6 (FIG. 14) and P7 (FIG. 1). A summary of the results are presented below in Table 1. Overall, the embodiments of the present invention which were tested demonstrated a significant advantage in hearing protection when compared to the standard ear protection. The decibel is commonly used in acoustics to quantify sound levels relative to a 0 dB reference which has been defined as a sound pressure level of 0.0002 microbar. The reference level is set at the typical threshold of perception of an average human and there are common comparisons used to illustrate different levels of sound pressure. As with other decibel figures, normally the ratio expressed is a power ratio (rather than a pressure ratio).

The human ear has a large dynamic range in audio perception. The ratio of the sound intensity that causes permanent damage during short exposure to the quietest sound that the ear can hear is greater than or equal to 1 trillion. Such large measurement ranges are conveniently expressed in logarithmic units: for example, the base-10 logarithm of one trillion ($10^{12}$) is 12, which is expressed as an audio level of 120 dB.

TABLE 1

The dB Change achieved in seven embodiments (1-7) of the present invention and the industry standard 3M ® headphone at selected frequencies (Hertz (Hz)).

|    | 125 Hz | 250 Hz | 500 Hz | 1000 Hz | 2000 Hz | 4000 Hz | 8000 Hz |
|----|--------|--------|--------|---------|---------|---------|---------|
| 3M | 9.5    | 6.3    | 8.9    | 23.2    | 34.2    | 45.2    | 21.6    |
| 1  | 3.7    | 1.2    | 2.1    | 20.5    | 21.3    | 30      | 60      |
| 2  | 9.6    | 10.1   | 14.5   | 32.1    | 32.1    | 41      | 60      |
| 3  | 6.1    | 3.3    | 4.9    | 18.2    | 29.5    | 60      | 60      |
| 4  | 3.2    | 4.8    | 26.8   | 23.7    | 33.3    | 60      | 60      |
| 5  | 5.3    | 5.4    | 12.1   | 25.8    | 29      | 60      | 60      |
| 6  | 10.5   | 5.3    | 21.1   | 19.5    | 39.5    | 60      | 60      |
| 7  | 8.9    | 5.8    | 18     | 15.3    | 23.7    | 60      | 60      |

Figure 15:
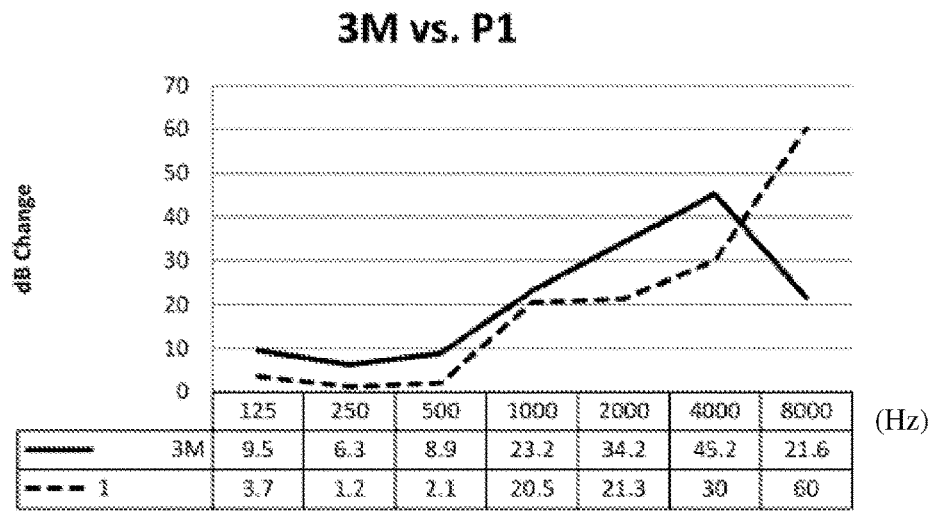
FIG. 15 illustrates a graph of dB Change vs. Frequency (Hz) for one embodiment of the present invention as shown in FIG. 11 and the industry standard 3M® headphone.

As illustrated in FIG. 15, there was significant sound absorption rates achieved in the 4000-8000 Hz range as indicated by the superior change in decibel levels detected by the dB Meter. The cellular scaffold of the present invention excelled above 3M®'s sound absorbing material in the 8000 Hz region by 40 dB. This type of protection is highly useful in dentistry as the drills used in this profession function at that frequency level.

Figure 16:
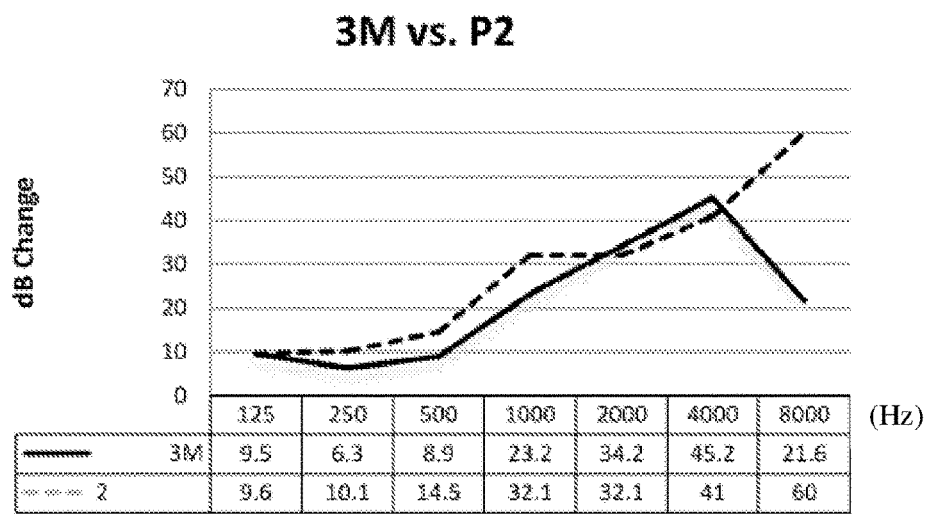
FIG. 16 illustrates a graph of dB Change vs. Frequency (Hz) for one embodiment of the present invention as shown in FIG. 3 and the industry standard 3M® headphone.
Figure 17:
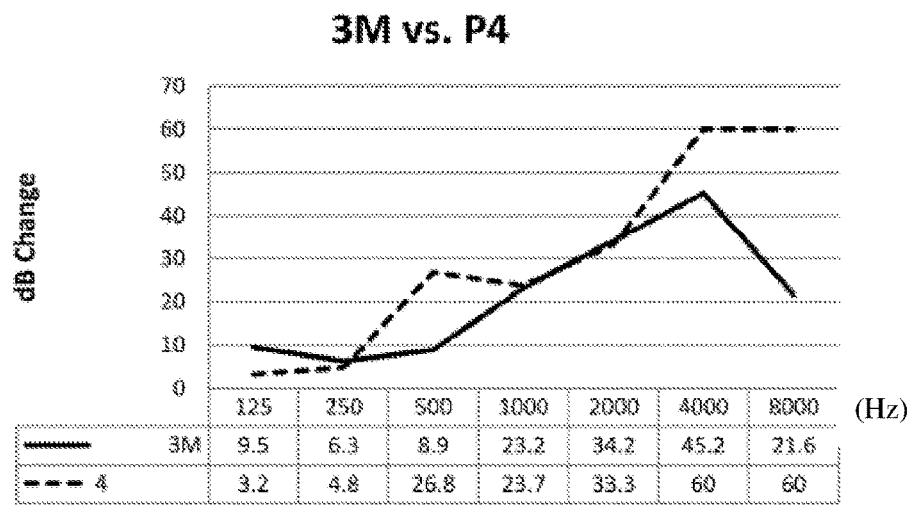
FIG. 17 illustrates a graph of dB Change vs. Frequency (Hz) for one embodiment of the present invention as shown in FIG. 13 and the industry standard 3M® headphone.

As illustrated in FIG. 16, there was significant sound absorption rates achieved in the 125-2000 and 4000-8000 Hz range of the cellular scaffold of the present invention when compared to the 3M® standard headphone sound absorbing material. The improved hearing protection in these frequency ranges would be an advantage to those in the construction industry and in professions where people are exposed to such high frequency tones. In FIG. 17 there was significant sound absorption rates achieved in the 250-1000 and 2000-8000 Hz range of the cellular scaffold of the present invention when compared to the 3M® standard headphone sound absorbing material. The improved hearing protection in these frequency ranges would be an advantage to those exposed to such high frequency tones.

Figure 18:
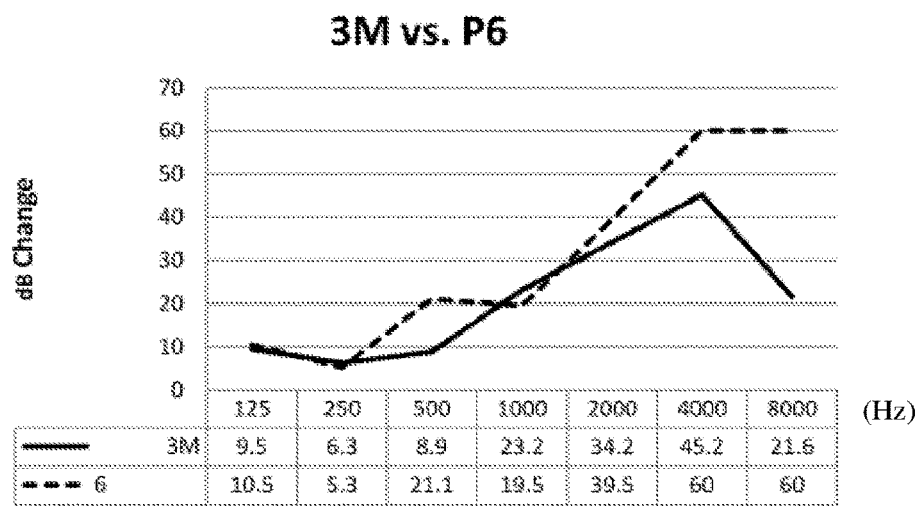
FIG. 18 illustrates a graph of dB Change vs. Frequency (Hz) for one embodiment of the present invention as shown in FIG. 14 and the industry standard 3M® headphone.
Figure 19:
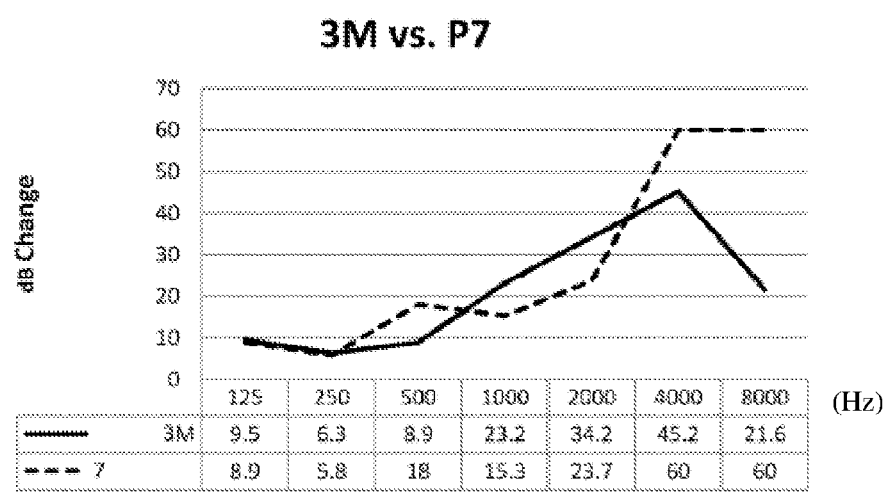
FIG. 19 illustrates a graph of dB Change vs. Frequency (Hz) for one embodiment of the present invention as shown in FIG. 1 and the industry standard 3M® headphone.

In FIG. 18, it is clearly demonstrated that there was significant sound absorption rates achieved in the 250-8000 Hz range of the cellular scaffold of the present invention when compared to the 3M® standard headphone sound absorbing material. Such a significant improvement in sound absorption within this frequency range would be a distinct advantage to those working in construction surrounded by low frequency tones and those exposed to high frequency tones. FIG. 19 clearly demonstrates that there was significant sound absorption rates achieved in the 250-500 and 2000-8000 Hz range of the cellular scaffold of the present invention when compared to the 3M® standard headphone sound absorbing material.

The 250-1000 Hz range is the range involved in many industrial hardware appliances and as such presents itself as a significant improvement in the area of personal protection within the construction industry. The 2000-8000 Hz range is an area of sound frequency which is related to high speed drills and electronic equipment. For example, dentists (and dental patients) are regularly at risk from high frequency drill sounds and as such, this improved protection is of significant value in this profession as a safety device. The results presented above clearly demonstrate that the sound absorbing material contained in a cellular scaffold of the present invention achieves significant improvements in sound absorption and hearing protection. Furthermore, the range of frequencies which the cellular scaffold of the present invention absorbs sound allows the user to hear conversations while dampening the harmful effects of, for example, drilling noises and the like.

This technology can also be applied to other forms of hearing protection. Individual earplugs can contain an insulating core that contains a sound absorbing material comprising a thixotropic material. Anechoic chambers can be constructed from panels of insulating material that would contain an internal structure of thixotropic material.

The invention is not limited to the embodiments hereinbefore described but may be varied in both construction and detail.

The invention claimed is:

1. A manufacture for use in a pair of headphones, wherein the manufacture comprises a sound-absorbing device that is configured to cover an ear, wherein the sound-absorbing device comprises both a sheet and a sound-absorbing material, wherein the sheet defines a cellular scaffold that comprises cells, wherein the sound-absorbing material comprises a thixotropic material that is located in the cells of the cellular scaffold, wherein the thixotropic material exhibits a low viscosity drop in response to low intensity noise and disproportionately high viscosity decrease in response to high intensity noise, wherein the thixotropic material has an apparent viscosity that decreases in response to constant sheer stress, and wherein the apparent viscosity gradually returns to equilibrium following removal of the sheer stress.

2. The manufacture of claim 1, wherein the sound-absorbing material is enclosed within an expandable container, and wherein the expandable container expands to allow an increase in volume of the thixotropic material.

3. The manufacture of claim 1, wherein the cellular scaffold comprises a honeycomb.

4. The manufacture of claim 1, wherein the cellular scaffold comprises a polymer film having cellular compartments, and wherein the thixotropic material is located within the cellular compartments.

5. The manufacture of claim 1, wherein the cellular scaffold comprises a plurality of tubes, each of which comprises first and second ends and a thixotropic material-containing lumen extending between the ends, wherein one end of each tube is disposed within a base.

6. The manufacture of claim 1, further comprising noise protection headphone that incorporates the sheet.

7. The manufacture of claim 6, wherein the headphone comprises a resiliently deformable portion, wherein, deformation of the resiliently deformable portion applies shear to the thixotropic material.

8. The manufacture of claim 1, wherein the thixotropic material is selected from the group comprising structured liquids, suspensions, emulsions, polymer solutions, aqueous iron oxide gels, vanadium pentoxide sols, starch pastes, pectin gels, flocculated paints, clays, soil suspensions, creams, drilling muds, flour doughs, flour suspensions, fibre greases, jellies, paints, honey, carbon-black suspensions, hydrophobically modified hydroxethyl cellulose, non-associative cellulose water solutions, flocculated polymer latex suspension, rubber solutions, metal slushes, bentonite clays, modified laponites, oils, lubricants, coal suspensions, xanthan gums, organic bentonite, fumed silica, aluminum stearate, metal soap, castor oil derivatives or thixotropic epoxy resin, or combinations thereof.

9. The manufacture of claim 1, wherein the sheet is circular.

10. A method of protecting an ear from high intensity noise comprising the step of placing a sound-absorbing device of the type adapted to cover the ears of a user and comprising a sound-absorbing material contained within a container in the form of a cellular scaffold, wherein the sound-absorbing material comprises a thixotropic material that is located in the cells of the cellular scaffold over and above the ear, wherein the thixotropic material has a resting viscosity which exhibits low resistance to passage of low intensity noise, and wherein the thixotropic material decreases in viscosity in response to incident high intensity noises to thereby exhibit high resistance to the high intensity noise.

* * * * *